United States Patent [19]

Cova et al.

[11] Patent Number: 4,867,849
[45] Date of Patent: Sep. 19, 1989

[54] PURIFICATION OF ALKYL GLYOXYLATE

[76] Inventors: Dario R. Cova, 723 Craig Dr., Kirkwood, Mo. 63122; John M. Thorman, 15558 Chequer Dr., Chesterfield, Mo. 63017

[21] Appl. No.: 224,045

[22] Filed: Jul. 25, 1988

[51] Int. Cl.[4] .......................... B01D 1/22; B01D 3/36; C07C 69/66
[52] U.S. Cl. ......................................... 203/28; 203/14; 203/67; 203/69; 203/72; 203/73; 203/80; 203/DIG. 19; 203/DIG. 25; 560/177; 560/186; 562/577
[58] Field of Search ................ 560/177, 186; 562/577; 203/28, 72, DIG. 25, 71, 73, 80, 89, DIG. 19, 14, 18, 19, 67, 69

[56] References Cited

U.S. PATENT DOCUMENTS

| | | | |
|---|---|---|---|
| 1,627,091 | 5/1927 | Haussler | 560/177 |
| 3,476,656 | 11/1969 | Van Tassell et al. | 203/72 |
| 4,144,226 | 3/1979 | Crutchfield et al. | 528/231 |
| 4,156,093 | 5/1979 | Christidis | 560/186 |
| 4,234,739 | 11/1980 | Photis et al. | 560/51 |
| 4,340,748 | 7/1982 | Baltes et al. | 560/177 |
| 4,502,923 | 3/1985 | Dyroff et al. | 203/71 |
| 4,692,547 | 9/1987 | Driscoll et al. | 560/186 |

FOREIGN PATENT DOCUMENTS

| | | |
|---|---|---|
| 130533 | 1/1985 | European Pat. Off. . |
| 176929 | 10/1982 | Japan . |
| 109221 | 3/1986 | Japan . |

OTHER PUBLICATIONS

"A Simple and Efficient Synthesis of Ethyl and Methyl Glyoxyate", James M. Hook, *Synthetic Communications*, 14(1), 83–87 (1984).

"A Convenient Preparation of Methyl and ethyl Glyoxylate", T. Kelly, T. Schmidt, J. Haggerty, *Synthesis*, Oct. 1972, pp. 544–545.

Primary Examiner—Wilbur Bascomb

[57] ABSTRACT

There is disclosed an improved process for the manufacture of glyoxylic acid obtained by oxidation of glycolic acid. For processing purposes alkyl esters of these acids are employed. Increased efficiency is obtained by recovering glycolate rich streams from one or more distillation operations and after treatment to remove acetic acid by-product the streams are recycled to the oxidation reaction.

23 Claims, 3 Drawing Sheets

PURIFICATION OF ALKYL GLYOXYLATE

BACKGROUND OF THE INVENTION

This invention relates to the manufacture of glyoxylic acid esters obtained by oxidation of the corresponding esters of glycolic acid and, more particularly, to an improved process for removing from said glyoxylic acid esters low concentrations of acetic acid other acids and hemiacetals formed in the manufacturing process as well as the efficient recovery of glycolic acid esters.

Polyacetal carboxylates have been demonstrated to be useful as builders in detergent formulations. Crutchfield U.S. Pat. No. 4,144,226 describes the preparation of polyacetal carboxylates by polymerization of an ester of glyoxylic acid, preferably methyl glyoxylate. The glyoxylic acid ester monomer may be prepared by vapor phase oxidation of the corresponding ester of glycolic acid. Side reactions occurring under the oxidation reaction conditions result in the contamination of the reaction product with water, an alkanol derived from the ester, and minor concentrations of acids such as acetic, formic, glycolic and glyoxylic as well as hemiacetals. To minimize the loss of yield to side reactions, the oxidation reaction is carried out with a deficiency of oxygen, so that the reaction mixture also contains a substantial fraction of unreacted glycolate ester.

In order to obtain a satisfactory yield and a high quality polyacetal carboxylate product from the polymerization reaction, it is necessary that the glyoxylate monomer be of high purity and that, in particular, it be purified to be substantially free of water, alkanol, carboxylic acids and unreacted glycolate ester. A typical process for recovering high quality glyoxylate ester is described in U.S. Pat. No. 4,502,923, wherein the product of the oxidation reaction is subjected to multiple distillation operations, first at low temperature under vacuum for removal of low boilers, primarily water and methanol, then at higher temperature under vacuum for removal of glycolate ester as an overhead stream, and finally at atmospheric pressure for removal of glyoxylate ester as an overhead stream. As indicated by an inflection in the vapor/liquid equilibrium curve, more glycolate ester can be removed from a mixture containing glyoxylate ester at low absolute pressure than at atmospheric pressure. The converse is true for glyoxylate ester. Bottoms from the glyoxylate atmospheric pressure distillation contain the glycolate that has not been removed as overhead in the glycolate vacuum still, as well as the hemiacetal of the glycolate and glyoxylate, and other high boilers. This stream is recycled to an earlier step in the process, typically the feed to the low boiler still.

Glyoxylate ester reacts with water to form the hydrate, and with both alkanol and glycolate to form the corresponding hemiacetals. These are equilibrium reactions which may proceed in either direction not only in the reaction step but also in the distillation steps and beyond. Although the first vacuum distillation step may be effective for removal of free water and alkanol, glyoxylate hydrate and glyoxylate/alkanol hemiacetal remain in the still bottoms and are carried forward to subsequent steps where they may dissociate to form additional free water and alkanol. Under the conditions of the atmospheric glyoxylate still, in particular, removal of glyoxylate ester from the liquid phase tends to promote the dissociation of hydrate and alkanol hemiacetal.

It has been discovered that upon incorporating into the process the various recycle streams necessary to provide an economic glyoxylate ester recovery system, acetic acid formed during the oxidation reaction accumulates in the system and preferentially exits with the glyoxylate ester. The resultant contamination of the glyoxylate ester causes a yield loss of methyl glyoxylate polymer since polymer endcaps formed by the acetic acid molecules are only temporary.

Furthermore, the accumulation of acetic acid increases the acidity of the system which in turn accelerates the autocatalytic decomposition of methyl glycolate and methyl glyoxylate, thereby reducing the recovery of those esters.

SUMMARY OF THE INVENTION

According to the present invention an improved process is provided whereby, in the separation of alkyl glyoxylate (monomer) from the reaction mass obtained by the oxidation of methyl glycolate, by one or more distillation operations, acetic acid as well as other acid components and hemiacetals are removed in a manner which avoids contamination of the glyoxylate ester without causing any loss in yield of such ester and provides improved recovery of alkyl glyoxylate ester.

In particular the improved process involves combining the glycolate rich stream from the monomer (glyoxylate ester) separation operation and at least a portion of the glycolate rich stream from a finishing distillation operation and returning, after treatment, the combined stream, which contains glycolate ester and acetic acid, to the oxidation operation. Typically the improved process comprises separating monomer from the glyoxylate/glycolate reaction mass by a first distillation, passing a glyoxylate rich stream from said first distillation to a second, finishing distillation to provide a second bottoms stream, combining a glycolate/glyoxylate containing bottoms stream from the monomer distillation with all, or a portion of the finishing distillation bottoms stream to an evaporation distillation operation to recover a glycolate/acetic acid stream which can be returned to the oxidation operation.

A further improvement in the process of the invention resides in the manner in which the evaporation operation of the combined bottoms stream is conducted. Preferably the evaporation operation comprises multi-step evaporations in which methyl glyoxylate content is reduced and the combined bottoms stream is evaporated to separate alkyl glycolate ester and acids which are recycled to the oxidation step.

DETAILED DESCRIPTION OF THE INVENTION

Figure 1:
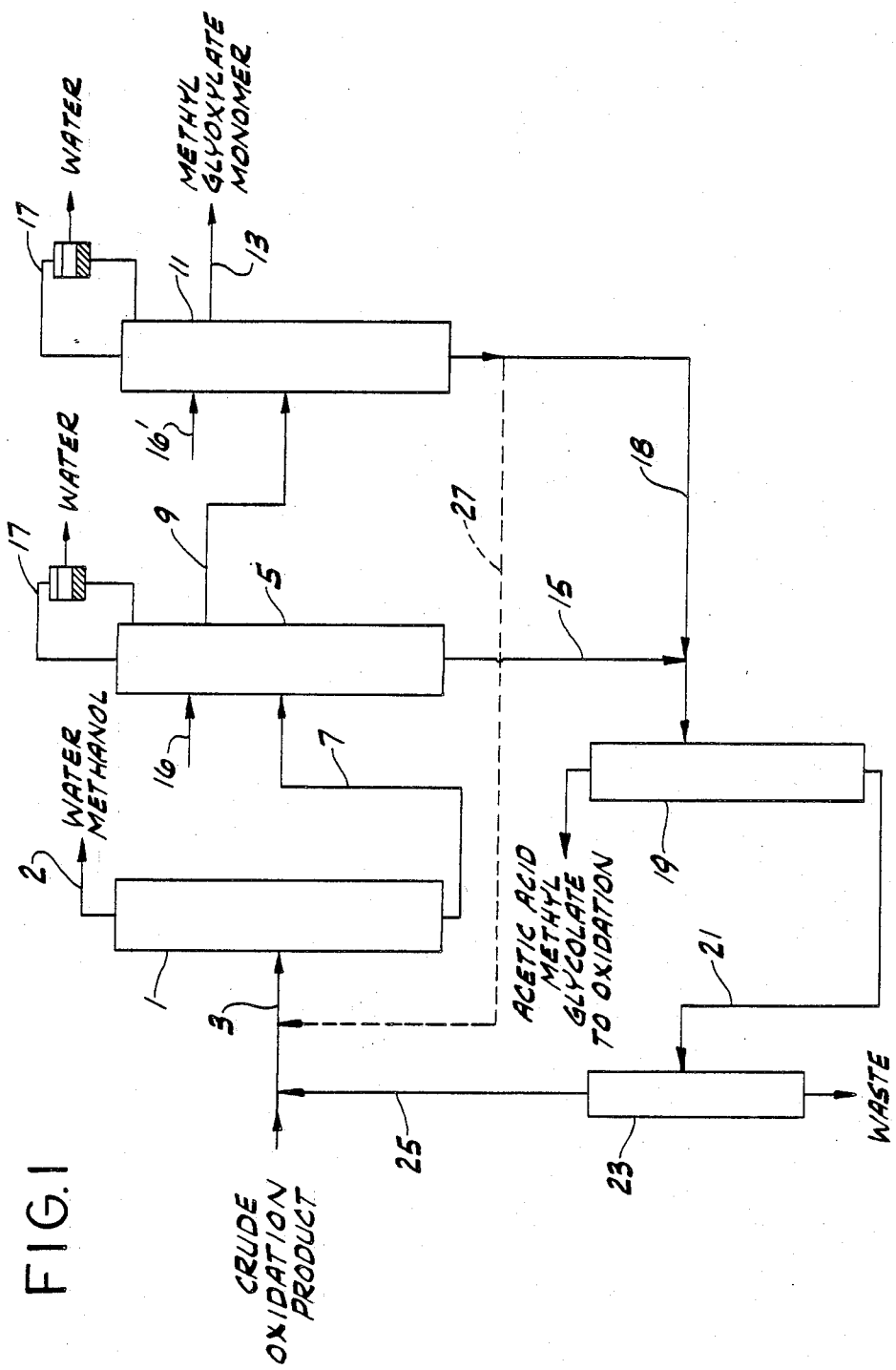
FIG. 1 is a schematic flow diagram illustrating the improved monomer (glyoxylate ester) separation process of the invention.

Briefly therefore, the present invention is directed to an improvement in a process for the preparation of an alkyl ester of glyoxylic acid having such quality as to be highly suited for the preparation of polyacetal carboxylate polymer. The process comprises oxidizing an ester of glycolic acid to the glyoxylic acid ester and producing a mixture comprising the glyoxylic acid ester, the glycolic acid ester, alcohol and water. Minor amounts of acids, such as acetic, formic, glycolic and glyoxylic are also present as well as hemiacetals. The crude reaction mixture is then distilled to remove the majority of low boilers. Glyoxylic acid ester is then recovered from the treated monomer mixture by a distillation operation, preferably an azeotropic distillation operation at atmospheric pressure. In the preferred distillation operation, the monomer mixture is fed to a multi-stage distillation column, in the upper stages of which a concentration of an azeotroping agent is maintained, the azeotroping agent forming a low boiling binary azeotrope with water and being immiscible with water to permit gravity separation of water from the agent. Vapor from the uppermost stage of the distillation column is condensed, thereby producing an overheads condensate. The azeotroping agent is separated from the water of the overheads condensate and returned above the uppermost stage of the monomer column as reflux. The glyoxylic ester fraction is removed from the side of the column at a stage intermediate the feed point and the uppermost stage; and a fraction comprising glycolic acid ester, glyoxylic acid ester hydrate and glyoxylic acid ester hemiacetals is removed from the bottom of the column.

Removal of residual water is substantially accomplished in the same atmospheric distillation operation in which the principal separation of glycolic acid ester from glyoxylic acid ester is carried out. However, to achieve maximum dryness the glyoxylic acid ester fraction is preferably fed to a third distillation column, the finishing column. In the finishing column a similar azeotropic distillation is carried out, again preferably at atmospheric head pressure for additional removal of residual moisture. The finishing column also effects separation of acetic acid and residual alkanol from the glyoxylic acid ester fraction, the acid and alkanol located in the bottoms fraction of the finishing column. This fraction also comprises glycolic acid ester, glyoxylic acid ester, ester hydrates, water, various other acids as described above, and hemiacetals. A concentration of azeotroping agent is maintained in the upper stages of the finishing column as described above with respect to the second distillation.

Because the reactions which form hydrate and hemiacetals in the oxidation step are reversible, there is no accumulation of hydrate or hemiacetals in the system, but instead almost all are ultimately converted to the desired glyoxylic acid ester product. Only the formation of high boilers, degradation from modest side reactions, and very minor losses to the atmosphere detract from essentially quantitative yield of the desired product.

Preferably combined bottoms fractions are first passed to a glycolate ester recovery operation which comprises passing the combined bottoms fractions to an evaporator, operated at below about 100 mm and preferably at about 10 mm pressure, wherein a glycolate ester/acid stream is taken as an overhead and returned to the oxidation operation. The bottoms from the evaporator are fed to a tar still where remaining glycolate ester and glyoxylate ester and also alkanol and water, are removed as an overhead stream and returned as feed to the low boilers treatment operation.

While in the process as described the total bottoms stream from the third distillation (finishing) column is combined with the bottoms stream from the second distillation (monomer) column, it is contemplated that the bottoms stream from the third (finishing) column can be split into two fractions, one fraction being combined with the bottoms stream from the monomer column and the other fraction serving as part of the feed to the first distillation operation. In such a scheme at least 25% of the bottoms stream from the third distillation step is combined with the bottoms stream from the second distillation step in order to insure a meaningful acid purge level.

Moreover, the process of the invention provides for the preparation of a high quality glyoxylic acid ester product in high yield without the necessity of operating with substantial excesses of gylcolic acid ester in the system as described in U.S. Pat. No. 4,502,923. Thus, both the productivity penalty and yield loss associated with the presence of excess glycolic acid ester are avoided. The process of the invention further provides high quality and high yield without the necessity of chemical reagents such as anhydrous phosphoric acid for conversion of the hemiacetal to the desired ester. The only foreign material in the system is the azeotropic agent, and this agent is highly volatile and readily separated from the glyoxylic acid ester.

A number of azeotroping agents may be used in carrying out the process of the invention. There are, however, certain criteria which govern the selection of the azeotroping agent. Thus, the agent should not be reactive with any of the components of the system, especially glyoxylic acid or the glyoxylic acid ester. It should not only be sufficiently immiscible in water to effect rapid and clean separation of the phases of the overheads condensate, but it should have limited solubility in water to minimize overheads losses and any environmental problems that might arise from its contamination of the overheads condensate water fraction, which is discarded. It should, of course, form a low boiling binary azeotrope with water, and also have an atmospheric boiling point sufficiently below that of the glyoxylic acid ester to provide for separation of water and ester.

Generally suitable azeotroping agents include aromatic hydrocarbons and halogenated alkanes. Particularly preferred is methylene chloride, but 1,1,1-trichloroethane and benzene are also advantageously used.

The process of the invention is especially advantageous in the preparation, isolation and purification of methyl glyoxylate. However, it is effective for the production of other lower alkyl glyoxylates in high yield and quality. In particular, the process may be used in the production of ethyl glyoxylate, n-propyl glyoxylate, isopropyl glyoxylate, and various butyl glyoxylates.

Although not a part of the purification process of this invention such a product is typically obtained when glycolic acid ester and air are fed continuously to a glycolic ester vaporizer thereby generating a vapor phase reactant mixture that is, in turn, fed to an oxidation reactor. The oxidation reaction produces a gaseous mixture of alkyl glyoxylate, alkyl glycolate, water, alkanol, carbon monoxide, carbon dioxide, residual oxygen, and nitrogen. This gaseous mixture is treated by passing it into a condenser from which the non-condensibles are vented, and where a condensed liquid phase mixture, comprising alkyl glyoxylate, alkyl glycolate, water, and alkanol is recovered.

FIG. 1 shows a system in which a crude alkylglycolate ester oxidation reaction product comprising alkyl glycolate, alkyl glyoxylate, water and alkanol is fed to a low boiler still 1 (first distillation) through line 3 where a major portion of the water and a substantial portion of alkanol are taken off under vacuum through line 2.

The bottom fraction from low boiler still 1 is fed through line 7 to a monomer still 5 (second distillation) operated under atmospheric pressure. The side draw 9 from column 5 is fed to a multi-stage finishing column 11 (third distillation) for recovery of glyoxlic ester. The side draw 13 from column 11 constitutes a dehydrated glyoxylic ester fraction suitable for the preparation of polyacetal carboxylate polymers. The second and third distillation steps are preferably performed with an azeotrope recovered by top condensers 17 which remove water and returns the azeotrope agent to the top of the column.

Bottoms from columns 5 and 11 are mixed thru lines 15 and 18 and fed to a recovery system comprising a glycolate recovery column 19 whereby glycolate is obtained as overhead and the bottoms fraction fed through line 21 to a tar column 23 to recover residual glyoxylate and glycolate as overhead. The overhead from column 23 can be returned to the system through line 25 for recovery.

The amount of bottoms from column 11 combined with bottoms fraction from column 5 is controlled by returning a portion of the bottoms from column 11 to column 1 through line 27. The feed to column 19 is typically composed of blends of from about 4:1 to about 6:1 of bottoms product from columns 5 and 11 respectively.

Typically, the feed mixture to the monomer still contains 40-50% by weight alkyl glyoxylate, 45-55% by weight alkyl glycolate, 1 to 2.5% by weight alkanol, and 0.3-1% water. The monomer still typically has 70 to 90 sieve trays and is preferably operated at atmospheric pressure, with a feed point between about the 40th and 60th tray. Operation at atmospheric pressure represents an optimal compromise between separation efficiency and degradation of product, since higher temperatures give a higher equilibrium factor of glyoxylate ester in the vapor phase but also conduce to thermal degradation of product. Where the top of the column is maintained at atmospheric pressure, the temperature at the bottom of the column is typically 150°-170° C. An azeotroping agent is concentrated in the top five to ten sieve trays of the column, with the temperature control point and azetroping agent makeup addition point being at about the fifth to tenth sieve tray through line 16. Vapor leaving the top sieve tray is essentially comprised of the binary azeotrope. Upon condensation, the moisture component of the azeotrope is drawn off and discarded while the azeotroping agent is returned to the top tray of the column as reflux. The side drawn glyoxylic acid ester fraction is taken at between about tray five and tray fifteen, but is in any case at least about five trays below the point for addition of makeup azeotroping agent. Between about 10% and about 50%, preferably about one third, of the liquid phase flowing to the side draw tray is continuously drawn off the column at that point as the glyoxylic acid ester fraction. For a feed mixture having the composition referred to above, the glyoxylic ester fraction may contain 85-95% by weight alkyl glyoxylate, 2-4% by weight alkyl glycolate, 3-7% by weight alkanol, and 0.3-1% water.

In addition, the monomer column 5 bottoms fraction, using a feed composition as described, may contain by weight, from 70% to 80% alkyl glycolate, 18% to 24% alkyl glyoxylate, 0.1% to 1% alkanol and 2% to 5% other acids.

Stages inside of the monomer column 5 can be established in any conventional manner as, for example, by bubble cap trays or sieve trays. However, in order to minimize decomposition of alkyl glyoxylate or alkyl glycolate during column operations, the residence time in the column is preferably kept to a minimum. Accordingly, sieve trays are preferred to bubble cap trays. The use of a packed column is particularly preferred because this provides the least liquid holdup and the shortest residence time. If packing is employed, the residence time inside the column can be limited to between about 4 and about 7 minutes, between about 8 and about 2 minutes in the stripping section. The use of packing also allows column pressure drop to be limited to between about 30 and about 77 mm Hg.

To minimize degradation of product, it is also important that oxygen be substantially excluded from the column during monomer still operation. Preferably, the column is purged with an inert gas, such as nitrogen, prior to column startup, and an inert gas blanket is maintained in the column during its operation.

Finishing column 11 typically contains between about thirty and about fifty sieve trays, with the feed point between about the 20th and 40th sieve tray. Like the monomer column, the finishing column is preferably operated at atmospheric pressure so that alkyl glycolate remaining in the feed stream is quantitatively separated from the glyoxylate fraction. Thus, temperature at the bottom of the column is in the range of 125°-150° C. The system at the upper portion of the column, i.e., above the feed sieve tray, is substantially identical to that for the monomer column. Thus, the azeotroping agent is concentrated in the top five to ten sieve trays of the column, with the temperature control point and azeotroping agent makeup addition point through line 16' being at about the fifth to tenth sieve tray. Vapor having a composition comprising the binary azeotrope is condensed and separated, with the azeotroping agent being refluxed to the top sieve tray of the column. The side draw for the dehydrated glyoxylic acid ester fraction is at between about sieve tray five and about sieve tray fifteen, and in any case at least about five sieve trays below the point at which makeup azeotroping agent is added. Between about 10% and about 50%, preferably about one-fourth of the liquid flowing to the side draw stage is removed as the side draw fraction. Oxygen is also excluded from this column, preferably by means of inert gas as described above with respect to the monomer column. Here also, sieve trays are preferred to bubble cap trays, and packed column is most preferred. By use of packing the residence time in finishing column 11 can be limited to about 5 minutes, no more than about 1 minute in the stripping section, and pressure drop through the column is limited to between about 20 and about 40 mm Hg.

For a feed stream from monomer column 5 containing 85-95% by weight alkyl glyoxylate, 2-4% by weight alkyl glycolate, 3–7% by weight alkanol, and 0.3–1% water, the finishing column is operated continuously to produce a dehydrated glyoxylic ester fraction containing 97–99% by weight glyoxylic acid ester, less the 0.2% by weight of combined water and alkanol, the balance being essentially constituted of the azeotroping agent. The bottom fraction from the finishing column comprises typically 75–85% by weight alkyl glyoxylate, 3–10% alkyl glycolate, 7–15% by weight alkanol, 0.1–1% acids, and less than 0.8% water.

The apparatus employed as the glycolate recovery column 19 in developing the process of the invention was a 50-mm I.D. wiped-film evaporator equipped with an external condenser. The evaporator had a non-jacketed borosilicate glass body with 5-mm thick wall. Heat input to the wiped surface was provided by a single electric heating mantle (340 watts). An identical mantle and local wire tracing were used to heat other parts of the apparatus. A constant-speed motor (450 rpm) rotated the wiper assembly. The carbon wipers were 8 inches long, notched to provide a downward flow bias. Residence time of material in the evaporator is estimated to vary from 7–30 seconds for the flow rates employed, based upon dye experiments. Likewise, the volume of liquid in the wiped-film region is estimated to be 0.8 cc.

Figure 2:
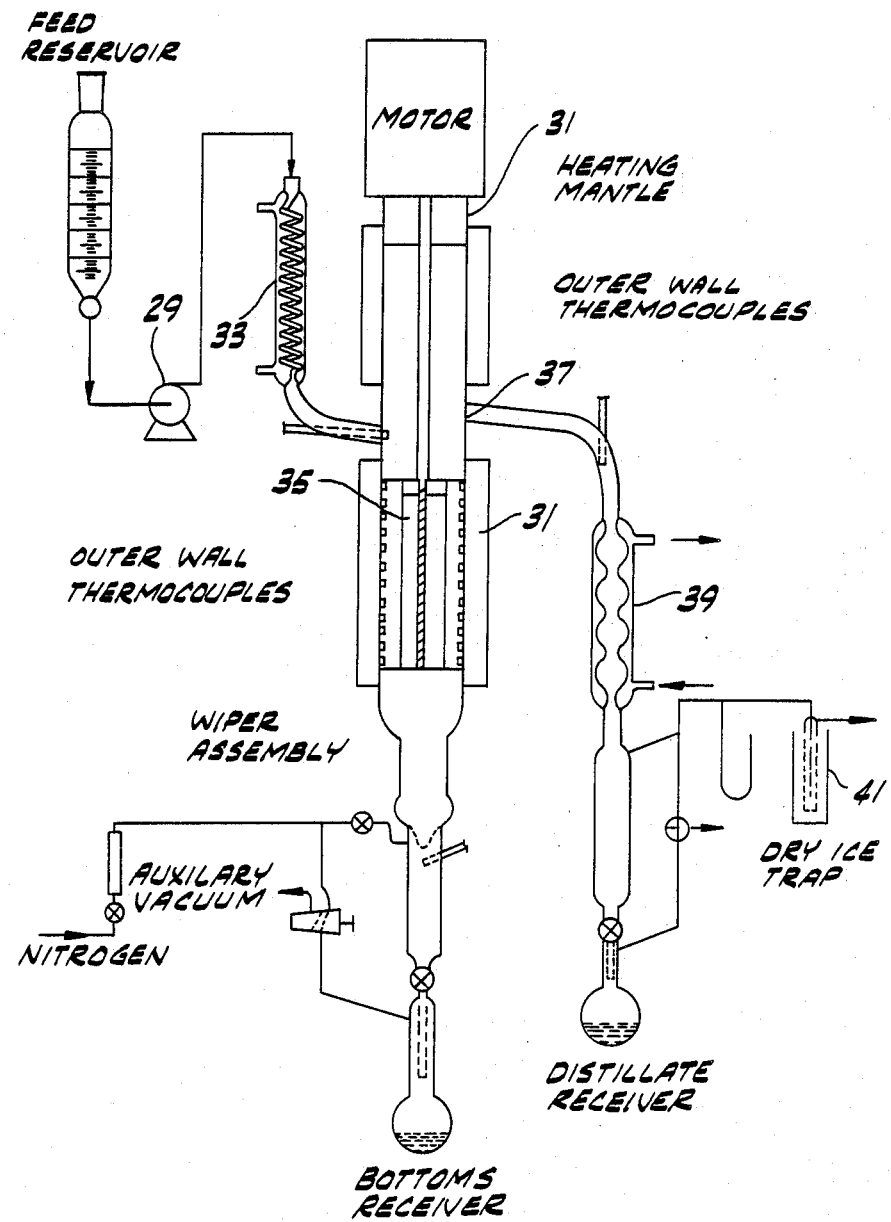
FIG. 2 is a schematic in partial section drawing of a laboratory scale glycolate column used to separate glycolate ester and acids from the bottoms fractions from the monomer and finishing columns.

A schematic of the apparatus is shown in FIG. 2. A peristaltic pump 29 delivered room temperature feed to the evaporator 31 at a fixed rate of 486 g/hr. Steady, smooth flow was provided by directing the feed downward through a Grahm (coil-type) condenser 33 connected to the evaporator feed port. The feed was not preheated and trickled down the interior evaporator wall to wipers 35. The vapor exit port 37 was located opposite the feed port. Vapors were routed directly (i.e., no reflux) to the external condenser 39 via an electrically traced line. Ambient-temperature cooling water was utilized in the condenser. An 11 mm Hg partial vacuum was drawn upon the system at a point immediately below the condenser. A nominal nitrogen purge (about 1.7 cc/min at STP) was introduced below the wiper assembly to prevent vapors from exiting the bottom of the evaporator. Vapors not liquified by condenser 39 were collected in a dry ice trap 41.

Various conditions were imposed upon the system. Distillate and bottom products were collected for 30 minutes upon reaching steady-state conditions. Product masses were determined gravimetrically. The mass flow rate of the feed was calculated using the feed density and change in feed reservoir volume during the 30 minute period. Samples were analyzed for components as shown in the following examples.

In the case of producing methyl glyoxylate, for example, the feed to the glycolate column is typically composed of, by weight, 61% methyl glycolate, 33% methyl glyoxylate, 2.9% methanol, 0.15% water and plus residual ingredients.

Figure 3:
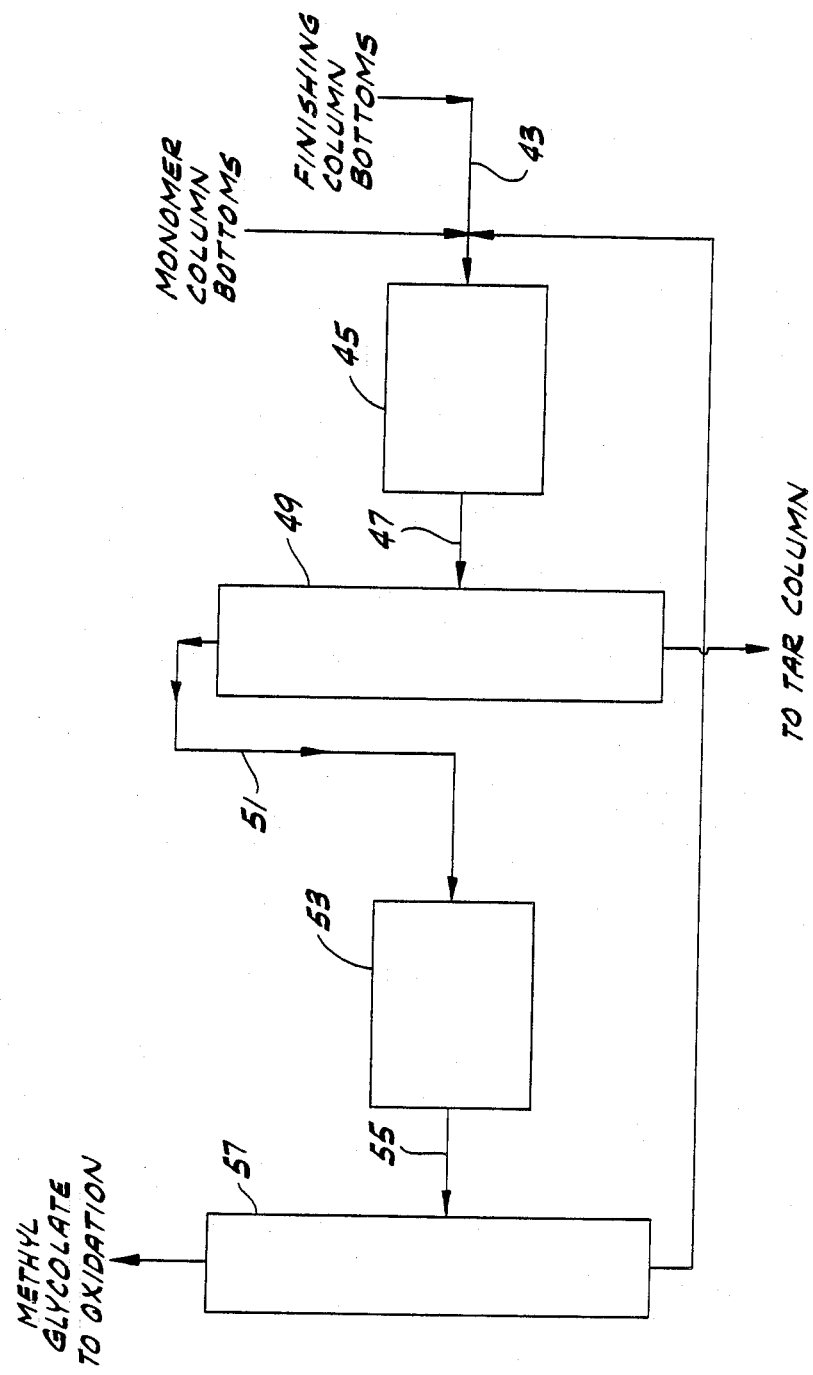
FIG. 3 is a schematic flow diagram illustrating a preferred process for methyl glycolate recovery which minimizes the amount of methyl glyoxylate recycled to the oxidation step.

More preferably the evaporation operation is conducted in multiple stages, as illustrated in FIG. 3. In FIG. 3 there is shown the preferred embodiment of this invention. Column bottoms from columns 5 and 11 are brought combined as shown through line 43 or separately if desired to holding tank 45. From tank 45 the bottoms are fed through line 47 to a first step evaporator 49 operated under vacuum. The overhead stream from evaporator 49 is fed through line 51 to a second holding tank 53 then through line 55 to a second step evaporator 57 also operated under vacuum. The overhead stream from column 57 contains a concentration of alkyl glycolate suitable for return to the oxidation step referred to above for the production of alkyl glyoxylate. The bottoms fraction from evaporator 49 is fed to a tar or residual recovery column such as described above with respect to FIG. 1 and the bottoms fraction from evaporator 57 is recycled to holding tank 45.

In the process of this invention it has been discovered that reduction of alkyl glyoxylate ester in the bottoms fraction is highly beneficial. The reduction of alkyl glyoxylate is most conveniently achieved by lowering the temperature of the bottoms fraction whereby a hemiacetal of glycolate and glyoxylate is obtained leaving the excess glycolate more easily removable. Because there is an equilibrium between free glycolate, glyoxylate and their hemiacetal complex it is therefore desirable to maintain the bottoms fractions at a temperature as low as possible during the evaporation step or steps.

Accordingly, the evaporation steps employed to remove the alkyl glycolate from the bottoms fraction are operated at low temperature and short retention times so as to maintain as much glyoxylate present in the form of a hemiacetal complex. Any reduction in temperature below that at which the bottoms fractions are delivered from columns 5 and 11 improve glycolate recovery efficiency.

In general, column bottoms fed to evaporator 49 is desirably below about 100° C. and more desirably below 70° C. Preferably the temperature of the column bottoms fed to evaporator 49 and 57 is about 55° C. Even ambient temperature is desirable if production scale, etc. economically permits such temperature reduction. Holding tanks 45 and 53 are employed to reduce the temperature of the feed to column 57 thereby maintaining the glyoxylate content at the lowest level suitable for large scale production.

To further maintain a major amount of glyoxylate in the hemiacetal complex form during the evaporation steps the evaporator is run at relatively low temperature and short retention time. Lower temperatures are achieved by conventional methods such as employing low pressure. Accordingly the evaporation steps are operated at a pressure below about 100 mm and preferably at about 10 mm and with retention times in the range of from about 3 minutes to about 7 seconds.

Another feature of the present invention is the elimination from the glyoxylate production system of low boiling acids which are by-products of the oxidation reaction. The most prevalent acid is acetic acid which has been found to build up concentration in prior art systems for the production of alkyl glyoxylate. The amount of acetic acid in the glyoxylate production system is controlled in accordance with this invention by returning at least a portion of the column bottoms from the finishing column 11 to the glycolate recovery system such s described above with respect to FIG. 3. Up to 98 percent of the acetic acid entering the system may be conveniently removed from the system in accordance with this invention.

To further illustrate the process of this invention there appears below the results of operational variations in the process of this invention indicating the optimum conditions for maximum glycolate recovery and acid elimination. Retention times are in minutes, all percent values are percent by weight, pressure expressed as mm Hg, and temperatures are in Centigrade scale. In performing the process of this invention a factor was observed which indicates the efficiency of operation for separating alkyl glycolate (Gc) from alkyl glyoxylate (Gx). The factor is termed a Separation Factor and is a proportion as follows:

$$\frac{\text{Separation}}{\text{Factor}} = \frac{Gx \text{ in bottoms}}{Gx \text{ in distillate}} \times \frac{Gc \text{ in distillate}}{Gc \text{ in bottoms}}$$

The Separation Factor is desirably high. In the following examples the apparatus in FIG. 2 was employed except where retention time is shown to be 2 minutes or above. In these runs a thermosyphon evaporator was employed with separate condenser in Example I-IC.

EXAMPLE I

Feed material was provided as described above and the retention time varied in the glycolate column. The product was analyzed and the results shown below. Methyl glyocolate (Gc) and glyoxylate (Gx) were produced.

TABLE I

| Effect of Retention Time on Separation | | | | | | |
|---|---|---|---|---|---|---|
| Retention Time | Pressure | Temp | GX in Feed | GX in Dist' | Fract'n Dist'd | Sep'n Factor |
| 0.1 | 13 | 58 | 21.3 | 2.1 | 0.51 | 37. |
| 2.3 | 10 | 70 | 20.2 | 8.2 | 0.51 | 6.4 |
| 2.7 | 10 | 71 | 20.9 | 7.5 | 0.51 | 7.7 |
| 2.8 | 10 | 59 | 20.3 | 5.8 | 0.53 | 9.4 |
| 0.1 | 100 | 101 | 20.0 | 15.1 | 0.50 | 2.1 |

The above data indicates lower retention time is desirable.

EXAMPLE II

In this example evaporator pressure is varied to show the desirable low pressure condition to produce desirably higher Separation Factors.

TABLE II

| Effect of Pressure on Separation | | | | | | |
|---|---|---|---|---|---|---|
| Retention Time | Pressure | Temp | Pct GX In Feed | Pct GX In Dist' | Fract'n Dist'd | Sep'n Factor |
| 0.1 | 13 | 63 | 21.3 | 9.6 | 0.67 | 9.0 |
| 0.1 | 100 | 101 | 21.2 | 14.0 | 0.71 | 5.0 |
| 2.3 | 100 | 101 | 20.0 | 15.1 | 0.50 | 2.1 |
| 2.6 | 20 | 84 | 21.2 | 12.8 | 0.50 | 4.4 |
| 2.8 | 10 | 59 | 20.3 | 5.8 | 0.53 | 9.4 |

EXAMPLE III

In this example the temperature of the feed to the evaporator is varied to demonstrate the advantage as shown by higher Separation Factors. In these runs the retention times were in the range of from 2.7 to 2.9 minutes.

TABLE III

| Effect of Feed Temperature On Separation | | | | | | |
|---|---|---|---|---|---|---|
| Feed Temp. | Pressure | Temp | GX In Feed | GX In Dist' | Fract'n Dist'd | Sep'n Factor |
| 158 | 10 | 70 | 20.0 | 13.1 | 0.58 | 3.1 |
| 22 | 10 | 59 | 20.3 | 6.18 | 0.54 | 9.0 |

The data in Table III shows the improved separation of glycolate when the temperature of the feed is lowered to provide conversion of the alkyl glyoxylate to alkyl glycolate - alkyl glyoxylate hemiacetal in the feed to the evaporator.

EXAMPLE IV

This example demonstrates two different types of evaporators having inherently different residence times.

TABLE IV

| Effect of Fractional Distillation on Separation | | | | | |
|---|---|---|---|---|---|
| Description of Apparatus | Top Pressure | GX In Feed | GX In Dist' | Fract'n Dist'd | Sep'n Factor |
| Fractionation column 15 ft of Koch-Sulzer packing reflux ratio range 2.5/1 to 1/1 | 20 | 21.8 | 1.0 | 0.44 | 60 |
| Wiped-Film still in 2 integrated steps 0.1 min retention time each step | 13 | 20.6 | 0.2 | 0.42 | 273 |
| Thermosyphon boilers in 2 integrated steps retention time 2.6 min each step | 10 | 20.0 | 0.8 | 0.46 | 71 |

Acetic Acid Removal

The component acid data in the following example indicate that acetic acid is removed via the distillate from the methyl glycolate removal operation (evaporator). For example approximately 98% of the incoming acetic acid is eliminated at the highest distillate/feed ratios tested. D/F=0.44. Even with D/F=0.14 about 60% removal is achieved. Furthermore, acetic acid accounts for over 90% of the acid present in the distillate, as glycolic acid and glyoxylic acid concentrate in the bottoms product. Formic acid at the 20 ppm level shows only a slight preference to go overhead, and disperses rather uniformly between the distillate and bottoms.

The acid analytical results can be deemed valid upon close examination. The trends in total acidity qualitatively and quantitatively compliment those of the component acids. The component acid balances in Table V leave very little doubt that acetic acid is concentrating in the distillate.

Acid concentrations in various streams was determined by ion chromatography.

EXAMPLE V

This example demonstrates the removal of acetic acid from the methyl glyoxylate production stream achieved in practice by combining the column bottoms from the third distillation step with column bottom from the second distillation. The feed to the evaporator was synthetic as noted above.

TABLE V

| Acetic acid Levels, ppm | | | Fract'n Dist'd | GX In Feed | GX In Dist' | Feed Temp | O/H Temp | O/H Press | Retent. time (sec.) |
|---|---|---|---|---|---|---|---|---|---|
| Feed | Dist' | Bottoms | | | | | | | |
| 870 | 3800 | 490 | 0.14 | 33.6 | 4.5 | 25 | 48-50 | 11 | 6 |
| 870 | 2600 | 255 | 0.28 | 33.6 | 4.6 | 25 | 49-51 | 11 | 6 |
| 870 | 2450 | 25 | 0.44 | 33.6 | 8.1 | 25 | 51 | 11 | 6 |

Separation Performance

The recovery of methyl glycolate in the distillate product is not diminished by the incorporation of finishing column bottoms product into the feed. The 63% recovery of methyl glycolate achieved in this investigation is similar to recoveries obtained in which the feed was only monomer column bottoms. Higher methyl glycolate recoveries can be anticipated at distillate/feed ratios greater than 0.44, but at the expense of more methyl glyoxylate and methanol carry-over.

The methanol concentration in the feed to the methyl glycolate recovery operation is a significant variable. Only 0.1–0.3 wt % methanol is inconsequential. However, almost 3 wt % methanol (i.e., combination of monomer column and finishing column bottom product), is substantial. This high level of methanol virtually eliminates the option of recycling the ensuing tar column distillate to the monomer column. Instead, the tar column distillate is routed to the low-boiler column as shown in FIG. 1, where a majority of the methanol can be purged.

The distillate product from the methyl glycolate removal step contains about 2–3 weight percent. The following example shows the unfavorable effect methanol has on glycolate separation employing an apparatus of FIG. 2.

EXAMPLE VI

The feed material to an evaporator of the type described in FIG. 2 was adjusted to control the amount of methanol. The results obtained appear in Table VI below.

TABLE VI

| | | Effect Of Methanol Level On Separation Factor | | | | | |
|---|---|---|---|---|---|---|---|
| Gx in Feed | Methanol in Feed | Fract'n Dist'd | Sep'n Factor | O/H Pressure | Feed Temp | O/H Temp | Retent' Time (sec) |
| 19.6 | 2.6 | 0.37 | 10.2 | 11 | 24 | n/a | 6 |
| | | 0.46 | 11.0 | | | n/a | |
| | | 0.56 | 11.0 | | | n/a | |
| 33.6 | 2.9 | 0.14 | 14.2 | 11 | 24 | 48–50 | 6 |
| | | 0.28 | 18.8 | | | 49–51 | |
| | | 0.44 | 14.9 | | | 51 | |
| 20.6 | 0.1 | 0.32 | 33.6 | 13 | 24 | 55 | 6 |
| | | 0.40 | 35.6 | | | 56 | |
| | | 0.49 | 39.1 | | | 57 | |
| 30.1 | 0.4 | 0.26 | 32.7 | 4 | 25 | 39 | 6 |
| | | 0.25 | 32.4 | | | 39 | |
| | | 0.31 | 30.8 | | | 39 | |
| 21.3 | 0.3 | 0.44 | 39.7 | 13 | 25 | 57 | 6 |
| | | 0.51 | 37.0 | | | 58 | |
| | | 0.57 | 24.8 | | | 60 | |
| | | 0.60 | 16.3 | | | 61 | |
| | | 0.67 | 9.3 | | | 63–64 | |

The results obtained in Example VI above shows the lower Separation Factors obtained with increasing amounts of methanol in the feed to the evaporator. The following example demonstrates that a two step evaporation procedure overcomes the problem.

EXAMPLE VII

In this example a synthetic feed stock was prepared for operation of the second evaporator step. However, the composition is typical of that obtained from the first evaporator step in the glycolate removal system as shown in FIG. 3 above.

TABLE VII

| Pct in Feed Composition | | | | | Pct In Dist' Composition | | | | | D/F | Pres-sure | Feed Temp | Dist' Temp | Ret time sec. | Sep. fact. |
|---|---|---|---|---|---|---|---|---|---|---|---|---|---|---|---|
| Water | Meth' | Gx | Gc | Other | Water | Meth' | Gx | Gc | Other | | | | | | |
| | | | | | | | First Step | | | | | | | | |
| 0.03 | 0.1 | 20.6 | 76.0 | 3.3 | 40.05 | 0.1 | 1.3 | 97.4 | 1.2 | 0.32 | 13 | 24 | 55 | 6 | 34 |
| | | | | | 40.05 | 0.1 | 1.5 | 97.1 | 1.3 | 0.40 | 13 | 24 | 56 | 6 | 36 |
| | | | | | 0.05 | 0.05 | 1.5 | 96.2 | 1.2 | 0.49 | 13 | 24 | 57 | 6 | 46 |
| | | | | | | | Second Step | | | | | | | | |
| 0.2 | 0.3 | 2.1 | 97.3 | 0.1 | 0.3 | 0.5 | 0.1 | 99.1 | 0.1 | 0.52 | 13 | 24 | 52 | 6 | 44 |
| | | | | | 0.2 | 0.3 | 0.2 | 99.2 | <0.1 | 0.84 | 13 | 24 | 53 | 6 | 70 |
| | | | | | 0.2 | 0.3 | 0.5 | 98.9 | <0.1 | 0.94 | 13 | 24 | 54 | 6 | 109 |

What is claimed is:

1. In a process for the recovery of alkyl glycoxylate form the reaction product obtained by the oxidation of alkyl glycolate, in which the reaction product is subjected to a series of distillation operations comprising a first distillation to remove alkanol and water as an overhead stream, a second distillation to separate alkyl gloxylate and a third distillation to remove residual water and alkanol from said alkyl gloxylate obtained from said second distillation, in which a first bottoms stream is removed from said second distillation and subjected to a glycolate evaporation operation in order to recover alkyl glycolate values, and in which a second bottoms stream is removed from said third distillation, the improvement which comprises, performing in independent order (1) reducing the temperature of said bottoms streams so as to reduce the alkyl gloxylate content by conversion of the gloyoxylate to alkyl glycolate-alkyl gloxylate hemiacetal and (2), combining at least about 25% of said second bottoms stream with said first bottoms stream to provide a combined bottoms stream and then subjecting said combined bottoms streams to low temperature and short retention time evaporation operation to provide an alkyl glycolate distillate stream.

2. A process of claim 1 in which the combined bottoms stream comprises a mixture of methyl glycolate, methylglyoxylate, methanol and acetic acid.

3. A process of claim 1 in which an azetropic agent is added and in which the distillations in the second and third distillations are azeotropic distillations.

4. A process of claim 1 in which said glycolate evaporation operation is a multi-step operation.

5. A process of claim 4 wherein the multi-step operation comprises two evaporation steps providing an overhead stream.

6. The process of claim 5 wherein the overhead stream from the first step is cooled before being fed to the 2nd evaporation operation.

7. A process of claim 1 wherein the 1st and 2nd bottoms streams are cooled to a temperature below 100° C.

8. A process of claim 1 wherein the 1st and 2nd bottoms streams are cooled to a temperature below about 70° C.

9. A process of claim 1 wherein the 1st and 2nd bottoms streams are cooled to about 60° C.

10. A process of claim 1 wherein the glycolate evaporation step is conducted at a pressure below about 100 mm.

11. A process of claim 1 wherein the retention time of the bottoms streams in the evaporation operation is below about 3 minutes.

12. A process of claim 1 wherein at least about 50% of the 2nd bottoms stream is combined with the 1st bottoms stream.

13. A process of claim 1 wherein the 1st and 2nd bottoms streams are combined prior to reducing the temperature, said temperature being reduced to not more than 100° C.

14. A process of claim 1 wherein the 1st and 2nd bottoms streams are reduced to a temperature below 100° C. prior to being combined.

15. In a process for the recovery of methyl glyoxylate monomer from a methyl glyoxylate containing mixture obtained by the oxidation of methyl glycolate in which the mixture is subjected to a series of distillation operations comprising the first distillation to remove methanol and water as an overhead steam, a second distillation to separate methyl glyoxylate monomer, and a third distillation to remove residual water and methanol from said methyl glyoxylate obtained from said second operation, said second and third distillations being azeotropic distillations by addition of an azeotrope in which a first bottoms stream is removed from said second distillation and subjected to a glycolate evaporation operation in order to recover methyl-glycolate values, and in which a second bottoms stream is removed from said third distillation, the improvement which comprises performing in independent order, (1) cooling said bottoms streams so as to reduce the methyl glycodylate content by conversion of said glyoxylate to a methyl glycolate-methyl hemiacetal, and (2) combining at least 25% of said second second bottoms stream with said first bottoms stream to provide a combined bottoms stream, and then subjecting said combined bottoms stream to a low temperature short retention time evaporation operation so as to retain a majority of said hemiacetal whereby a methyl glycolate-rich distillate is obtained.

16. A process of claim 15 in which evaporation operation is a multi-step operation.

17. A process of claim 15 wherein the methyl glycolate distillate stream is cooled after the first step and prior to the second evaporation step.

18. A process of claim 15 wherein the bottoms streams are cooled to a temperature below about 100° C.

19. A process of claim 18 wherein the temperature of the bottoms streams are reduced to a temperature below 100° C. after being combined.

20. A process of claim 19 wherein the temperature of the bottoms streams are reduced to a temperature below about 70° C.

21. A process o 19 wherein the temperature of the bottoms streams are reduced to a temperature of about 60° C.

22. A process of claim 15 wherein the evaporation operation is conducted at a pressure below about 100 mm.

23. A process of claim 15 wherein the evaporation operation is conducted so as to provide a retention time in the range of from about 0.1 to about 3 minutes.

* * * * *